(12) United States Patent
Feldman et al.

(10) Patent No.: US 12,013,342 B2
(45) Date of Patent: *Jun. 18, 2024

(54) APPARATUS AND METHODS FOR ENDOMETRIAL TISSUE IDENTIFICATION

(71) Applicant: Research Development Foundation, Carson City, NV (US)

(72) Inventors: Marc D. Feldman, San Antonio, TX (US); Thomas E. Milner, Irvine, CA (US); Andrew G. Cabe, San Antonio, TX (US); Arnold D. Estrada, Austin, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/050,902

(22) Filed: Oct. 28, 2022

(65) Prior Publication Data

US 2023/0324302 A1 Oct. 12, 2023

Related U.S. Application Data

(63) Continuation of application No. 17/223,265, filed on Apr. 6, 2021, now Pat. No. 11,506,607, which is a
(Continued)

(51) Int. Cl.
*G01J 3/26* (2006.01)
*A61B 5/00* (2006.01)
*G01N 21/64* (2006.01)

(52) U.S. Cl.
CPC ....... *G01N 21/6486* (2013.01); *A61B 5/0071* (2013.01); *G01N 21/6456* (2013.01);
(Continued)

(58) Field of Classification Search
CPC .......... G01N 21/6486; G01N 21/6458; G01N 2021/6417; G01N 21/6456;
(Continued)

(56) References Cited

U.S. PATENT DOCUMENTS 4,852,579 A * 8/1989 Gilstad ................. A61B 10/00
250/483.1
5,079,262 A 1/1992 Kennedy et al.
(Continued)

FOREIGN PATENT DOCUMENTS

JP 6-102458 4/1994
JP 11-511048 9/1999
(Continued)

OTHER PUBLICATIONS

Barkan et al., "Morphologic features of endometriosis in various types of cytologic specimens", *Diagnostic Cytopathol.*, 41(11):936-942, 2013.
(Continued)

*Primary Examiner* — Abdullahi Nur
(74) *Attorney, Agent, or Firm* — Parker Highlander PLLC

(57) ABSTRACT

Exemplary embodiments of the present disclosure include apparatus and methods to identify endometrial tissue.

17 Claims, 10 Drawing Sheets
(7 of 10 Drawing Sheet(s) Filed in Color)

Related U.S. Application Data continuation of application No. 16/849,938, filed on Apr. 15, 2020, now Pat. No. 11,009,465, which is a continuation of application No. 15/981,101, filed on May 16, 2018, now Pat. No. 10,663,403.

(60) Provisional application No. 62/506,910, filed on May 16, 2017.

(52) U.S. Cl.
CPC ........ *G01N 21/6458* (2013.01); *A61B 5/0082* (2013.01); *G01N 2021/6417* (2013.01); *G01N 2021/6478* (2013.01)

(58) Field of Classification Search
CPC ............ G01N 2021/6478; G01N 33/02; A61B 5/0071; A61B 5/0082; A61B 18/22; A61B 5/00; A61B 6/00; A61B 1/00; A61B 1/227
See application file for complete search history.

(56) References Cited

U.S. PATENT DOCUMENTS

| | | | |
|---|---|---|---|
| 5,211,938 A | 5/1993 | Kennedy et al. | |
| 5,769,791 A * | 6/1998 | Benaron | A61B 17/3417 600/476 |
| 7,383,076 B2 | 6/2008 | Ntziachristos et al. | |
| 9,195,043 B2 * | 11/2015 | Ghosh | A61B 90/20 |
| 9,482,513 B2 | 11/2016 | Feldman et al. | |
| 10,663,403 B2 | 5/2020 | Feldman et al. | |
| 2007/0038126 A1 | 2/2007 | Pyle et al. | |
| 2010/0292543 A1 | 11/2010 | Levitt et al. | |
| 2011/0213252 A1 | 9/2011 | Fulghum | |
| 2011/0301441 A1 * | 12/2011 | Bandic | A61B 5/4875 600/306 |
| 2012/0326055 A1 * | 12/2012 | Wilson | A61B 5/0059 250/459.1 |
| 2013/0211391 A1 * | 8/2013 | BenYakar | A61B 18/20 606/10 |
| 2015/0087902 A1 | 3/2015 | Mertz et al. | |
| 2016/0078309 A1 | 3/2016 | Feldman et al. | |
| 2016/0135891 A1 * | 5/2016 | Feldman | A61B 18/20 606/3 |
| 2017/0100073 A1 | 4/2017 | Trujillo et al. | |

FOREIGN PATENT DOCUMENTS

| | | |
|---|---|---|
| JP | 2013-066559 | 4/2013 |
| JP | 2016-515032 | 5/2016 |
| WO | WO 1997/006724 | 2/1997 |
| WO | WO 2014/030344 | 2/2014 |
| WO | WO 2014/152961 | 9/2014 |

OTHER PUBLICATIONS

Boppart et al., "High resolution imaging of endometriosis and ovarian carcinoma with OCT: feasibility for laparoscopic-based imaging", *Br. J. Ob. Gynecol.*, 106:1071-1077, 1999.

Buchweitz et al., "Detection of peritoneal endometriotic lesions by autofluorescence laparoscopy", *Am. J. Obstetrics Gynecol.*, 195:949-954, 2006.

Burney and Giudice, "Pathogenesis and pathophysiology of endometriosis", *Fertility and Sterility*, 98(3):511-519, 2012.

Demco, "Laparoscopic Spectral Analysis of Endometriosis", *J. Am. Assoc. Gynecol. Laparoscop.*, 11(2):219-222, 2004.

Duong et al., "A multispectral LED array for the reduction of background autofluorescence in brain tissue", *J. Neurosci. Methods*, 220(1):46-54, 2013.

Extended European Search Report issued in European Application No. 18801351, dated Dec. 23, 2020.

Gegzna et al., "Methods for Autofluorescence Analysis of Uterine Cavity Washings", *Lithuanian J. Phys.*, 55(1):63-70, 2015.

Hariri et al., "Laparoscopic optical coherence tomography imaging of human ovarian cancer", *Soc. Gynecol. Oncol.*, 114(2):188-194, 2009.

Küpker et al., "Autofluoreszenz und Endometriose", English translation appended, *Gynäkologe*, 40:349-355, 2007.

Marcoux et al., "Laparoscopic surgery in infertile, women with minimal or mild endometriosis", *New Engl. J. Med.*, 337(4):217-222, 1997.

Office Action issued in Australian Application No. 2018270943, dated May 17, 2022.

Office Action issued in Japanese Application No. 2019-563226, dated Apr. 5, 2022, and partial English translation.

Office Action issued in Japanese Application No. 2019-563226, dated Apr. 20, 2023, and partial English translation.

Office Action issued in U.S. Appl. No. 15/981,101, dated Sep. 17, 2019.

Office Action issued in U.S. Appl. No. 16/849,938, dated Sep. 11, 2020.

Office Action issued in U.S. Appl. No. 17/223,265, dated Apr. 12, 2022.

Office Action issued in European Application No. 18801351, dated Jan. 12, 2023.

Office Action issued in Korean Application No. 10-2019-7037195 dated Jan. 3, 2023.

PCT International Search Report and Written Opinion issued in corresponding PCT Application No. PCT/US2018/032877, dated Jul. 30, 2018.

Shalini et al., "Imaging Tools for Endometriosis: Role of Ultrasound, MRI and Other Imaging Modalities in Diagnosis and Planning Intervention", Chapter 24 In: Endometriosis, Basic Concepts and Current Research Trends, ed. Chaudhury K., pp. 437-446, 2012.

Ushenko et al., "Laser polarization-variable autofluorescence of the network of optically anisotropic biological tissues: Diagnostics and differentiation of early stages of cancer of cervix uteri", *J. Innov. Optical Health Sci.*, 7(3):1-10, 2014.

Vaitkuviene et al., "Chemomertical analysis of endometrial tissue fluorescence spectra", *Proc. SPIE*, 4903:240-245, 2002.

Vlek et al., "Laparoscopic Imaging Techniques in Endometriosis Therapy: An apparatusatic Review", *J. Minimally Invasive Gynecol.*, 23(6):886-892, 2016.

\* cited by examiner

APPARATUS AND METHODS FOR ENDOMETRIAL TISSUE IDENTIFICATION

CROSS-REFERENCE TO RELATED APPLICATIONS

This application is a continuation of U.S. application Ser. No. 17/223,265, filed Apr. 6, 2021, which is a continuation of U.S. application Ser. No. 16/849,938, filed Apr. 15, 2020, now U.S. Pat. No. 11,009,465, which is a continuation of U.S. application Ser. No. 15/981,101, filed May 16, 2018, now U.S. Pat. No. 10,663,403, which claims priority to U.S. Provisional Patent Application Ser. No. 62/506,910 filed May 16, 2017, the contents of each of which are incorporated by reference herein.

BACKGROUND INFORMATION

Endometrial tissue in the abdomen of women is typically difficult to identify and remove. This difficulty can pose a significant problem, with eighteen percent of all women affected by endometriosis. In general, there is a greater potential for pain reduction and improved fertility with an increase in the removal of diseased tissue. Multiple surgeries are typically needed due to incomplete identification, and implants on important structures, e.g. ovaries, are not removed. Diagnosis of endometriosis typically requires histologic confirmation of the markers stroma, hemosiderin, and glands, and samples for the confirmation of endometriosis can be obtained through laparoscopic surgery and biopsy.

Computed tomography (CT), magnetic resonance imaging (MRI) or ultrasound typically cannot identify lesions. Instead, the lesions are confirmed with surgical biopsies, and of the removed tissue, only eighty percent is typically diseased. The existing endometriosis identification techniques therefore include many shortcomings, and improved apparatus and methods are desired.

Accordingly, improved imaging apparatus and methods would aid in the detection of endometrial tissue.

SUMMARY

Exemplary embodiments of the present disclosure include apparatus and methods to detect optical properties of endometriosis to improve surgical removal. Exemplary apparatus and methods disclosed herein can identify endometrial tissue via the endogenous fluorescence of hemosiderin when subjected to excitation light. In particular embodiments, imaging with two-photon luminescence (TPL) apparatus can be used to reveal the endogenous fluorescence of hemosiderin associated with endometrial tissue.

Certain embodiments may also utilize imaging techniques to identify glands associated with endometrial tissue. Glands are one of the markers for endometriosis and an imaging target for optical coherence tomography (OCT) due to the voids the glands can create.

Exemplary embodiments of the present disclosure include apparatus and methods for detecting endometrial tissue. Particular embodiments include a method of detecting endometrial tissue, where the method comprises: illuminating tissue with excitation light; detecting an endogenous fluorescence emission from a portion of the tissue in response to illuminating the tissue with the excitation light; and identifying the portion of the tissue producing the endogenous fluorescence emission as endometrial tissue.

In particular embodiments, the excitation light is emitted from a light emitting diode (LED). In specific embodiments, the excitation light has a wavelength of 450 nm. In certain embodiments, the endogenous fluorescence emission is detected by a camera, and in particular embodiments the endogenous fluorescence emission passes through a filter before being detected by the camera. In some embodiments, the filter is a gradient-index (GRIN) lens, and in specific embodiments the GRIN lens is configured to filter light below 550 nm. In particular embodiments, the camera comprises a complementary metal-oxide-semiconductor (CMOS) sensor.

In particular embodiments, the excitation light has a wavelength between 370 and 510 nanometers (nm) for single photon luminescence. For embodiments using two photon luminescence, the excitation light has a wavelength between 740 and 1020 nanometers (nm). In some embodiments, the endogenous fluorescence emission has a wavelength between 550 and 750 nanometers (nm). In specific embodiments, the endogenous fluorescence emission is emitted from hemosiderin.

In certain embodiments, the excitation light is emitted from a laser. In some embodiments, the excitation light is emitted from a light source configured for use in a multi-photon imaging apparatus, and in specific embodiments the excitation light is emitted from a light source configured for use in a two-photon imaging apparatus.

Certain embodiments of the method further comprise identifying a void created by an endometrial gland. In particular embodiments, the void is identified by optical coherence tomography.

Exemplary embodiments also include an apparatus comprising: an excitation light source configured to emit excitation light having a wavelength between 450 and 490 nanometers (nm), where the excitation light source is configured to illuminate a portion of tissue; and an imaging device configured to detect endogenous fluorescence emission light having a wavelength between a wavelength between 590 and 650 nanometers (nm).

In certain embodiments, the excitation light source is a light emitting diode (LED), and in particular embodiments the LED is configured to emit excitation light with a wavelength of 450 nm. In specific embodiments, the imaging device is a camera. Certain embodiments further comprise a filter configured to filter the endogenous fluorescence emission before the endogenous fluorescence emission is detected by the camera. In some embodiments, the filter is a gradient-index (GRIN) lens, and in specific embodiments the GRIN lens is configured to filter light below 550 nm. In particular embodiments, the camera comprises a complementary metal-oxide-semiconductor (CMOS) sensor.

Certain embodiments further comprise a computer processor configured to analyze the endogenous fluorescence emission light and classify the endogenous fluorescence emission light as an indicator of endometrial tissue. Particular embodiments further comprise an optical coherence tomography (OCT) imaging device, and in some embodiments the OCT imaging device is configured to detect a void in the portion of tissue.

Specific embodiments further comprise a computer processor configured to analyze the void in the tissue and classify the void as an indicator of an endometrial gland. In certain embodiments, the excitation light source is a light emitting diode (LED) and in particular embodiments the excitation light source is a laser. In some embodiments, the excitation light source is a component in a multi-photon imaging apparatus, and in specific embodiments the excitation light source is a component in a two-photon imaging apparatus. In certain embodiments, the excitation light source and the imaging device are contained within a photonic crystal fiber.

In the following, the term "coupled" is defined as connected, although not necessarily directly, and not necessarily mechanically.

The term "optical coherence tomography light source" or "OCT light source" is defined as a light source configured for use in an optical coherence tomography (OCT) imaging apparatus.

The term "multi-photon light source" or "MPL light source" is defined as a light source configured for use in multi-photon o tomography (OCT) imaging apparatus.

The term "two-photon light source" or "TPL light source" is defined as a light source configured for use in two-photon (TPL) imaging apparatus.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The invention may be better understood by reference to one of these drawings in combination with the detailed description of specific embodiments presented herein.

DETAILED DESCRIPTION OF ILLUSTRATIVE EMBODIMENTS

Figure 1:
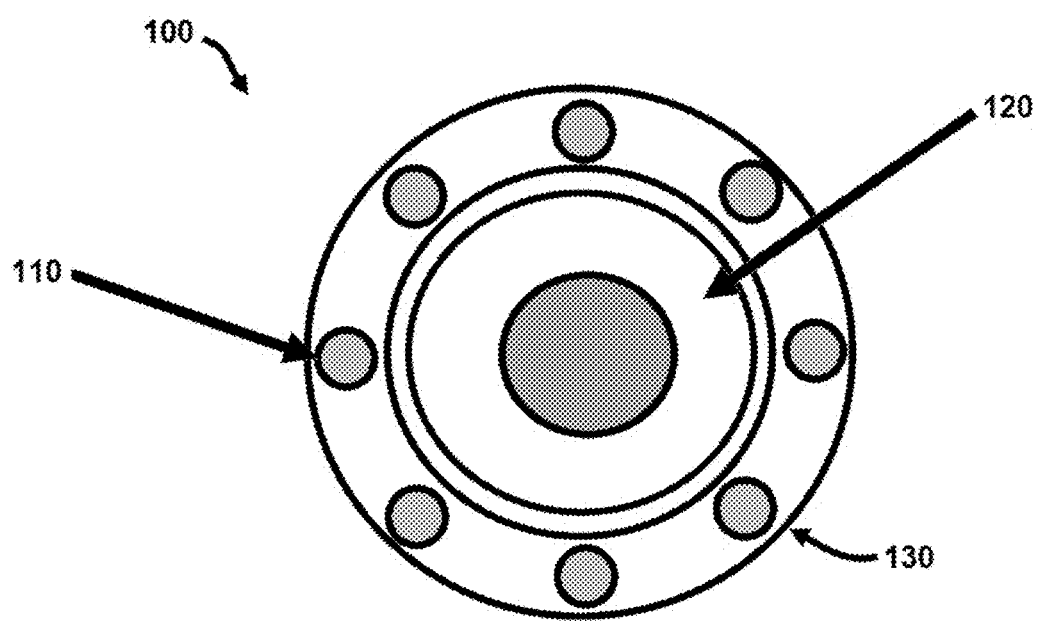
FIG. 1 shows a schematic of an end view of an apparatus according to an exemplary embodiment of the present disclosure.
Figure 2:
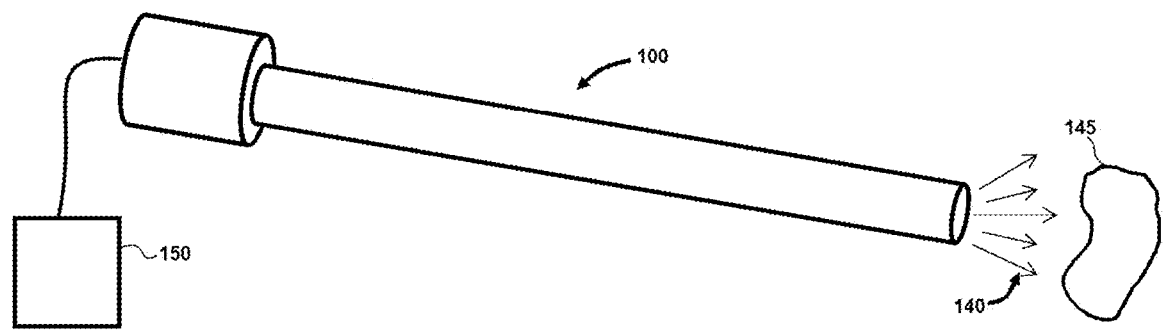
FIG. 2 shows side view of the device of FIG. 1.

Referring now to FIGS. 1 and 2, an apparatus 100 comprises an excitation light source 110 configured to emit excitation light 140 to illuminate a portion of tissue 145. In addition, apparatus 100 comprises an imaging device 120 configured to detect endogenous fluorescence emission light. In certain embodiments, excitation light source 110 and imaging device 120 may be contained within a photonic crystal fiber (PCF) 130. In certain embodiments, excitation light source 110 may be a light source configured for use in a two-photon luminescence (TPL) imaging apparatus. In particular embodiments, aspects of imaging apparatus 100 may include elements of the apparatus disclosed in U.S. Pat. No. 9,482,513, the entire contents of which are incorporated herein by reference.

During use, apparatus 100 can be operated to illuminate tissue with excitation light and detect endogenous fluorescence emission light that is associated with endometrial tissue. For example, in certain embodiments, apparatus 100 may comprise a computer processor 150 configured to analyze the endogenous fluorescence emission light and classify the endogenous fluorescence emission light as an indicator of endometrial tissue. In exemplary embodiments, computer processor 150 can be configured to execute the analysis and classification of the endogenous fluorescence emission light via a software contained in a non-transitory computer readable medium.

In particular embodiments, light source 110 may be configured to emit excitation light 140 having a wavelength between 370 and 510 nm or more preferably between 450 and 490 nm for single photon luminescence. For embodiments using two photon luminescence, the excitation light has a wavelength between 740 and 1020 nanometers (nm) or more preferably between 900 and 980 nm. In addition, imaging device 120 may be configured to detect emission light having a wavelength between 550 and 750 nm or more preferably between 590 and 650 nm. As disclosed further below, apparatus 100 can be used to illuminate a portion of tissue and identify endometrial tissue in the portion of illuminated tissue. In exemplary embodiments, apparatus 100 can be used in vivo to identify endometrial tissue for removal.

Figure 3:
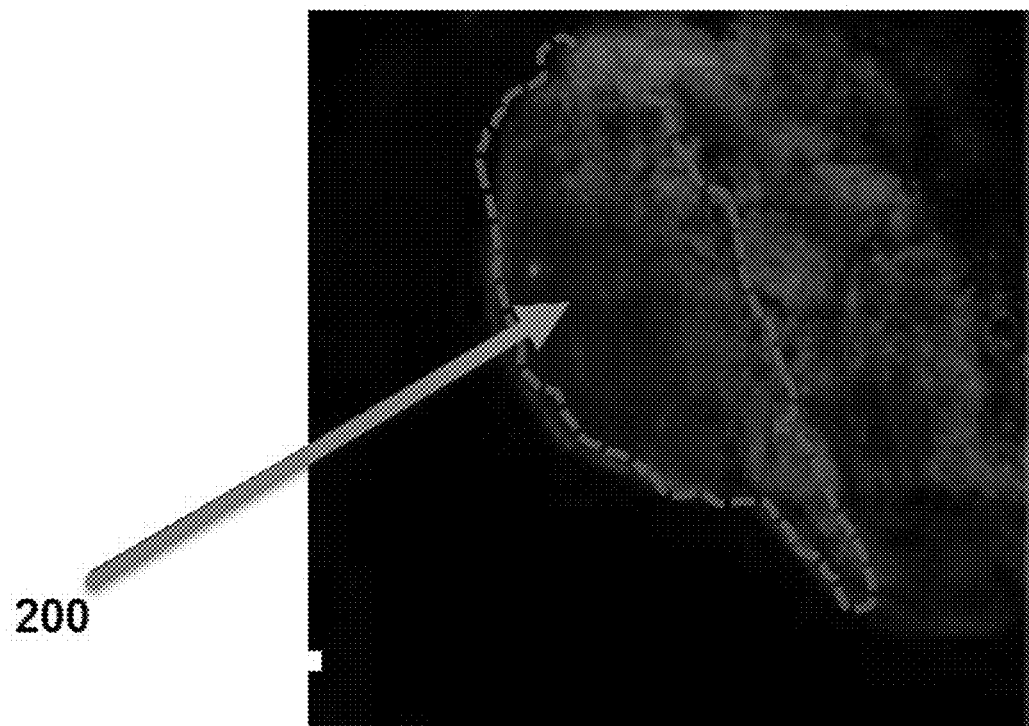
FIG. 3 shows a tissue image obtained with an apparatus according to an exemplary embodiment of the present disclosure.
Figure 4:
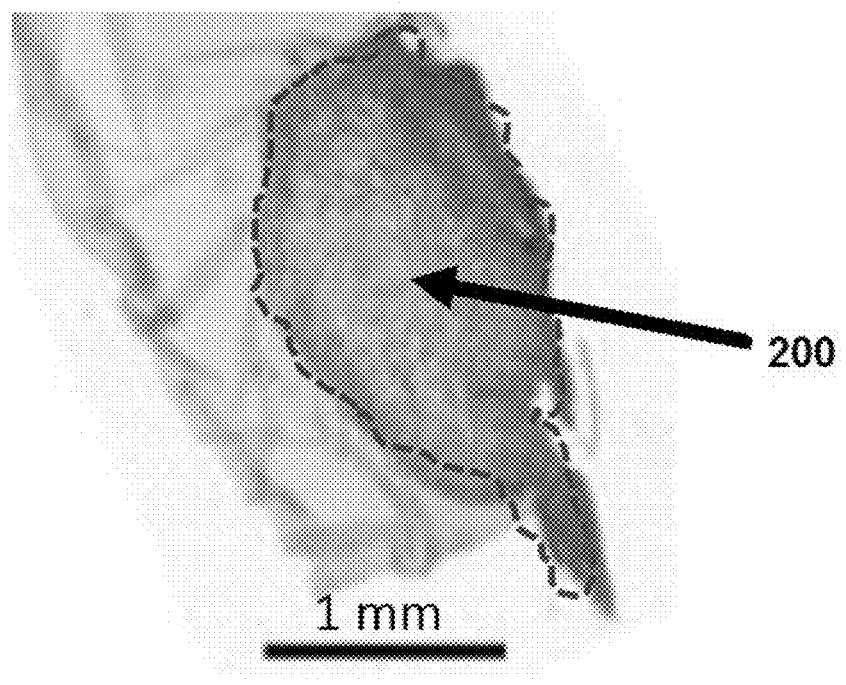
FIG. 4 shows illustrates a hematoxylin and eosin stain (H&E) stain of tissue in the image shown in FIG. 3.

Referring now to FIG. 3, an image obtained with an imaging apparatus as disclosed herein illustrates red fluorescence from hemosiderin 200, an indicator of endometrial tissue. FIG. 4 illustrates a hematoxylin and eosin stain (H&E) stain of the hemosiderin 200 located in FIG. 3. As shown in the figures, the stain indication in FIG. 4 correlates with the red fluorescence shown in FIG. 3.

Figure 5:
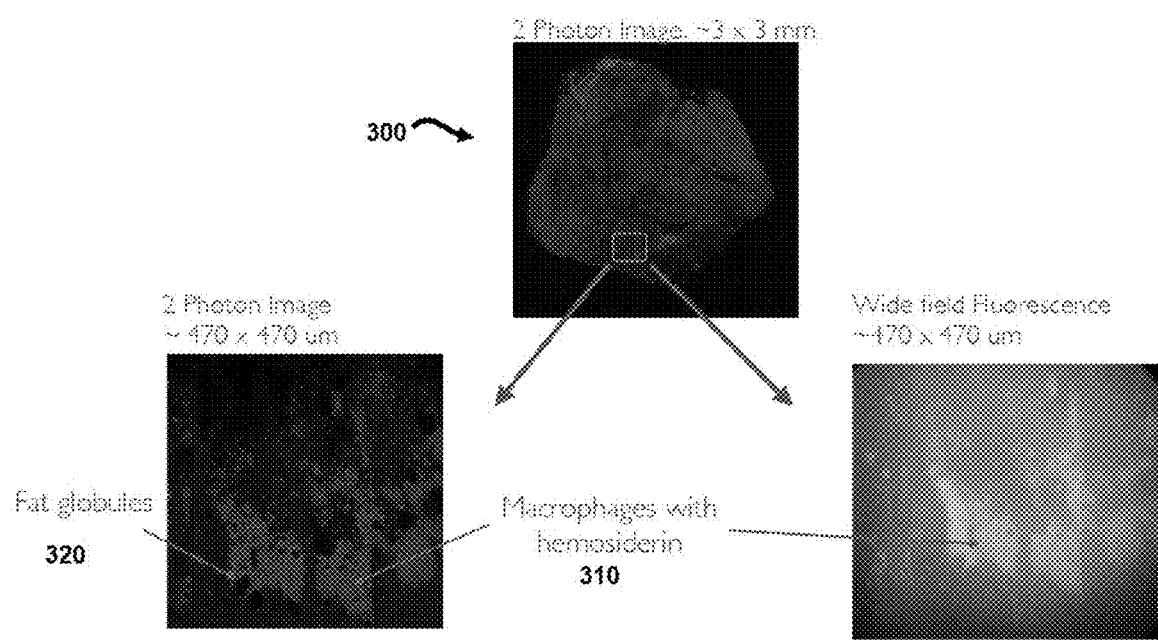
FIG. 5 shows a tissue image obtained with a device according to an exemplary embodiment of the present disclosure.

FIG. 5 illustrates a two-photon luminescence (TPL) image 300 of a region approximately 3 millimeters by 3 millimeters. The expanded view in the lower left portion of FIG. 5 illustrates a TPL image of a region of image 300 that is approximately 470 µm by 470 µm containing fat globules 320. The lower right portion of FIG. 5 illustrates a wide field fluorescence view of the 470 µm by 470 µm region showing macrophages 310 with hemosiderin.

Figure 6:
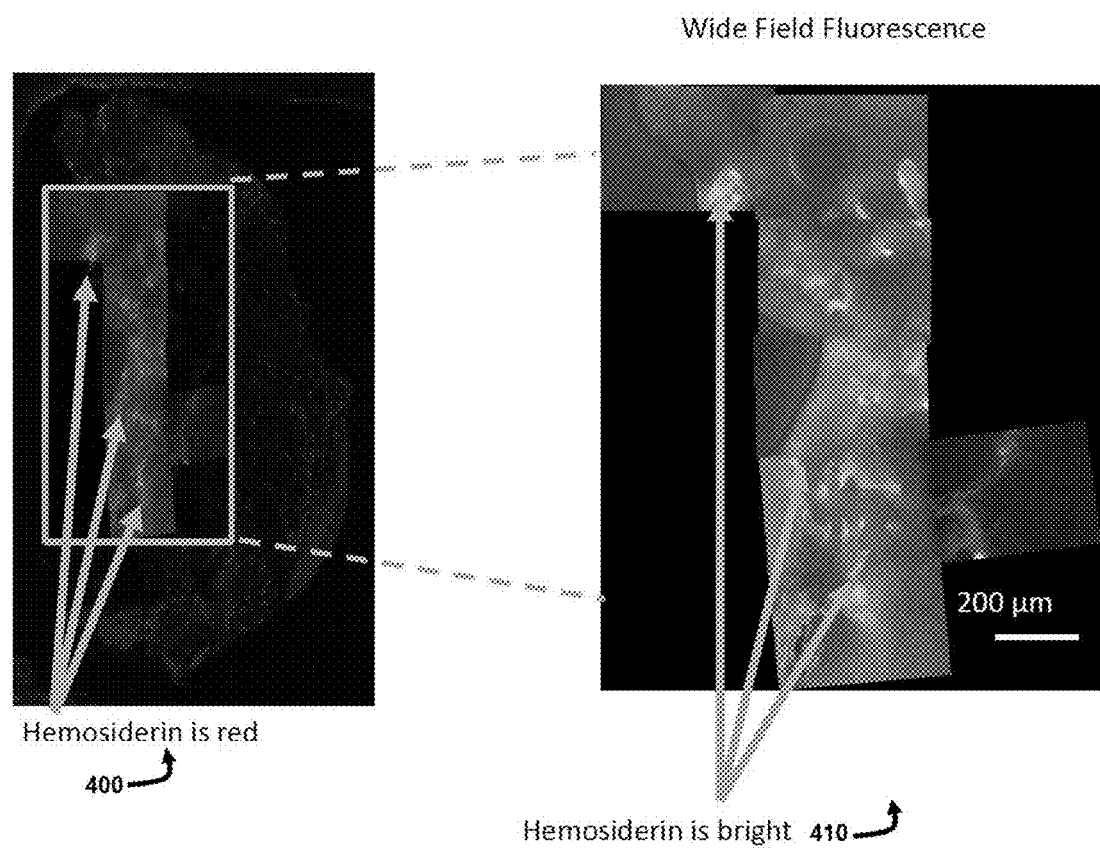
FIG. 6 shows a tissue image obtained with a device according to an exemplary embodiment of the present disclosure.

FIG. 6 illustrates a two-photon luminescence (TPL) image 400 and a wide field fluorescence image 410. As shown in the figure, hemosiderin is visible in red in image 400 and as bright white light in image 410.

Figure 7:
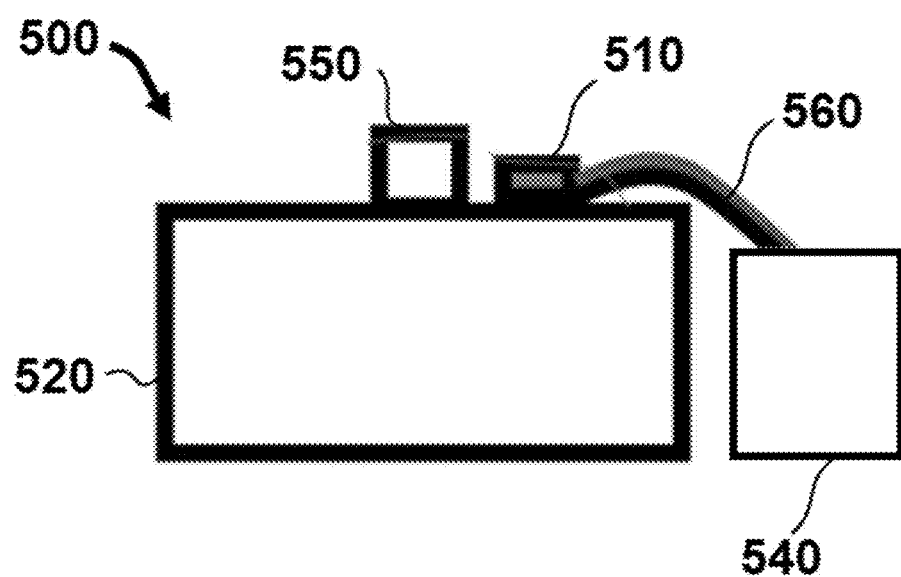
FIG. 7 shows a schematic of an apparatus according to an exemplary embodiment of the present disclosure.

FIG. 7 illustrates a schematic of an exemplary embodiment of the present disclosure. This embodiment operates under principles generally equivalent to the previously-described embodiments. However, the embodiment in FIG. 7 can be constructed with components having reduced manufacturing costs. For example, apparatus 500 comprises an imaging device 520 that is a relatively inexpensive camera module utilizing a complementary metal-oxide-semiconductor (CMOS) or charge coupled device (CCD) sensor. In a specific embodiment, imaging device 520 may be a Raspberry Pi Camera module. In addition, apparatus 500 may comprise a filter 550 configured to filter light that is detected by imaging device 520. In certain embodiments, filter 550 may be configured as a gradient-index (GRIN) lens configured to filter light below a particular wavelength. In one specific embodiment, filter 550 is a GRIN lens configured to filter light below 650 nm.

In addition, apparatus 500 comprises a light source 510 configured to emit excitation light. In particular embodiments, light source 510 is an LED light source configured to emit light in a range between 370 nm and 510 nm. In the specific embodiment shown, light source 510 is an LED light source configured to emit light at a wavelength of approximately 450 nm. In the embodiment shown, apparatus 500 also comprises a power supply 540 configured to provide power to light source 510 and imaging device 520 via electrical connector 560.

During operation, apparatus 500 can be operated in a manner similar to previously-described embodiments. Specifically, light source 510 can be used to emit excitation light at a frequency selected to reveal the endogenous fluorescence of hemosiderin associated with endometrial tissue (e.g. 450 nm). When the light emitted from light source 510 is directed to tissue that includes hemosiderin, the portions of the tissue containing hemosiderin will fluoresce. Specifically, the hemosiderin will fluoresce at a frequency (e.g. less than 550 nm) that will pass through filter 550 and be detected by imaging device 520.

Figure 8:
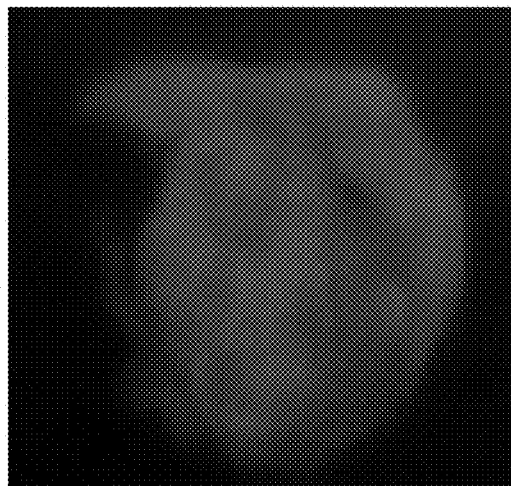
FIGS. 8-10 show a comparison of tissue images obtained with an apparatus according to an exemplary embodiment of the present disclosure.
Figure 8:
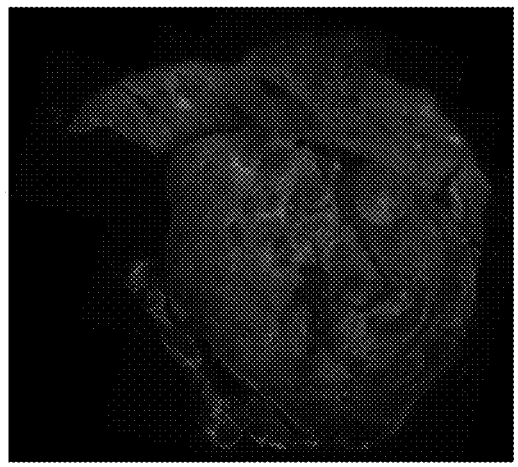
Figure 9:
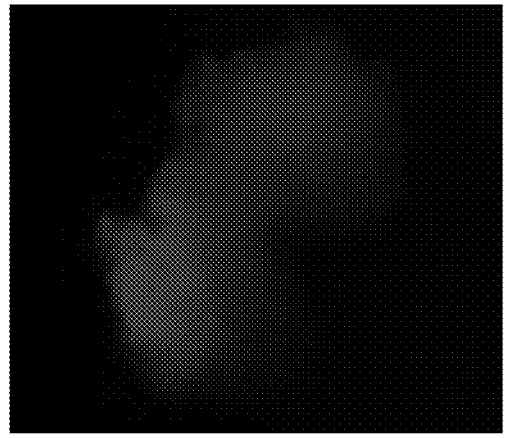
Figure 9:
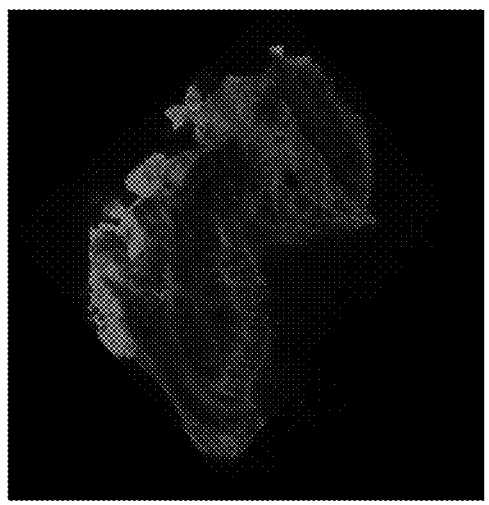
Figure 10:
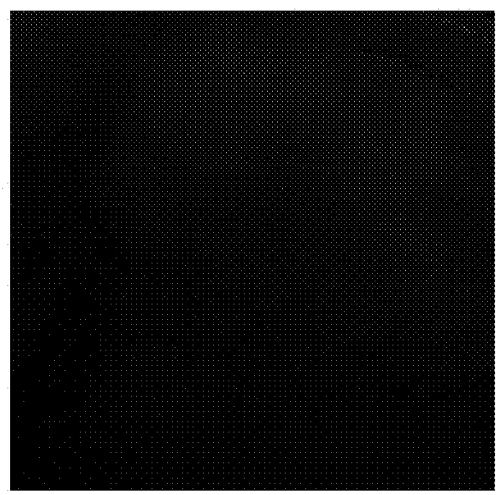
Figure 10:
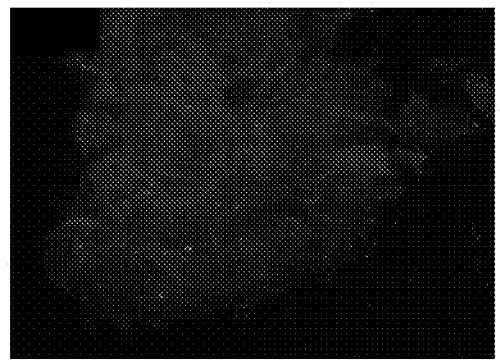

FIGS. 8-10 illustrate a comparison of imaging data obtained with the embodiment shown in FIG. 7 with that of a two-photon microscope. The images were obtained from samples prepared in an agar-gel cube, as described more fully in the working example description provided below. While FIGS. 8 and 9 illustrate samples with positive indications of endometrial tissue, FIG. 10 illustrates a sample that does not include indications of endometrial tissue.

As shown in the figures, the embodiment shown in FIG. 7 was able to produce imaging data that correlated well with that of the two-photon microscope. In each of the figures, the top image is the image obtained with the embodiment of FIG. 7, and the bottom image is the image obtained with a two-photon microscope. In the top images obtained with the embodiment of FIG. 7, the red portions of the image indicate hemosiderin associated with endometrial tissue. In the bottom images obtained with the two-photon microscope, the red indications of endometrial tissue are overlayed with blue (indicating connective tissue), resulting in endometrial indications that vary from pink to red with blue overlays. As shown in FIGS. 8 and 9, the indications in the top images correlate well with the indications in the bottom images. This demonstrates that the positive endometrial indications were successfully identified with the embodiment shown in FIG. 7.

FIG. 10 similarly demonstrates the lack of positive indications for both the embodiment of FIG. 7 and the two-photon microscope embodiment in a sample that did not contain endometrial tissue. This demonstrates the embodiment of FIG. 7 did not produce false positives.

The images obtained by apparatus disclosed herein (including those illustrated in FIGS. 3, 5, 6, and 8-10, for example) can be used to aid in the detection of endometrial tissue. The disclosed apparatus can therefore be employed to allow a user to identify endometrial tissue and distinguish it from healthy (e.g. non-endometrial tissue). This can allow a user of the disclosed apparatus to minimize patient trauma by removing endometrial tissue while minimizing the removal of healthy tissue. It can also reduce the amount of time that a patient is subjected to surgical procedures. Accordingly, the apparatus and methods disclosed herein provide substantial benefits over existing techniques for the identification of endometrial tissue.

All of the devices, apparatus and/or methods disclosed and claimed herein can be made and executed without undue experimentation in light of the present disclosure. While the devices, apparatus and methods of this invention have been described in terms of particular embodiments, it will be apparent to those of skill in the art that variations may be applied to the devices, apparatus and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

WORKING EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure Research methods have been implemented to co-register endometrial tissue to histological truth through several imaging steps. The first step was to embed them in agar-gel cube to stabilize position and prevent tissue deformation and dehydration. This agar remains around the tissue from imaging to histology, allowing three-dimensional co-registration to aid in identify unique optical properties of OCT and TPL targets in endometriosis validated by histology and a OB/GYN pathologist.

Twenty-three patients were consented and fourteen were identified by the surgeon at time of operation as having endometriosis. N=68 samples were analyzed. Surgical assessment of tissue thought to be endometriosis had a positive predictive value (PPV) of 73% and a negative predictive value (NPV) of 93%. On the same samples TPL has a PPV of 100% and NPV 100% in the 81% of samples where hemosiderin is present.

OCT has had a PPV of 100% and a NPV of 94% in 33% of samples where glands are present. Both glands seen by OCT and hemosiderin seen by TPL improve a surgeon's ability to correctly diagnose endometriosis. Accordingly, these imaging techniques can add value by increasing PPV, allowing for the removal of less healthy tissue and shortening the operative procedure.

REFERENCES

The contents of the following references are incorporated by reference herein:
U.S. Pat. No. 5,079,262
U.S. Pat. No. 5,211,938
U.S. Pat. No. 9,482,513
"Detection of peritoneal endometriotic lesions by autofluorescence laparoscopy", Buchweitz, American Journal of Obstetrics and Gynecology (2006) 195, 949-54.
"Laparoscopic Spectral Analysis of Endometriosis", Demco, The Journal of the American Association of Gynecologic Laparoscopists, May 2004, Vol. 11, No. 2.
"Laparoscopic Imaging Techniques in Endometriosis Therapy: An apparatusatic Review", Vlek, Journal of Minimally Invasive Gynecology 2016.
Autofluoreszenz and Endometriose, Küpker, Gynäkologe 2007 40:349-355.
Marcoux S, et al. (1997) Laparoscopic surgery in infertile, women with minimal or mild endometriosis. *New England Journal of Medicine* 337(4):217-222.
Shalini Jain Bagaria, Rasalkar D D, & Paunipagar B K (2012) Imaging Tools for Endometriosis: Role of Ultrasound, MRI and Other Imaging Modalities in Diagnosis and Planning Intervention. *Endometriosis, Basic Concepts and Current Research Trends*, ed Chaudhury K).
Burney R O, Giudice L C. Pathogenesis and pathophysiology of endometriosis. *Fertility and Sterility.* 2012, 98(3), 511-519.
Boppart S A, Goodman A, Libus J, Pitris C, Jesser C A, Brezinski M E, Fujimoto J G. High resolution imaging of endometriosis and ovarian carcinoma with OCT: feasibility for laparoscopic-based imaging. *British J Ob Gyn* 1999, 106, 1071-1077.

The invention claimed is:

1. A method of detecting endometrial tissue, the method comprising:
    illuminating tissue with excitation light;
    detecting an endogenous fluorescence emission from a portion of the tissue in response to illuminating the tissue with the excitation light; and
    identifying the portion of the tissue producing the endogenous fluorescence emission as endometrial tissue, wherein:
        the excitation light is emitted from a light emitting diode (LED);
        the endogenous fluorescence emission is detected by a camera;
        the endogenous fluorescence emission passes through a filter before being detected by the camera; and
        the endogenous fluorescence emission is emitted from hemosiderin.

2. The method of claim 1 wherein the excitation light has a wavelength of 450 nm.

3. The method of claim 1 wherein the filter is a gradient-index (GRIN) lens.

4. The method of claim 3 wherein the GRIN lens is configured to filter light below 550 nm.

5. The method of claim 1 wherein the camera comprises a complementary metal-oxide-semiconductor (CMOS) sensor.

6. The method of claim 1 wherein the excitation light has a wavelength between 370 and 510 nanometers (nm).

7. The method of claim 6 wherein the method incorporates single photon imaging of the tissue.

8. The method of claim 6 wherein the excitation light has a wavelength between 740 and 1,020 nanometers (nm).

9. The method of claim 8 wherein the method incorporates two-photon imaging of the tissue.

10. The method of claim 1 wherein the endogenous fluorescence emission has a wavelength between 550 and 750 nanometers (nm).

11. The method of claim 1 further comprising identifying a void created by an endometrial gland.

12. The method of claim 11 wherein the void is identified by optical coherence tomography.

13. An apparatus comprising:
    an excitation light source configured to emit excitation light having a wavelength between 370 and 510 nanometers (nm) or between 740 and 1,020 nm, wherein the excitation light source is configured to illuminate a portion of tissue;
    a filter;
    an imaging device configured to detect endogenous fluorescence emission light having a wavelength between a wavelength between 550 and 750 nanometers (nm), wherein:
        the excitation light source is a light emitting diode (LED);
        the imaging device is a camera; and
        the filter is configured to filter the endogenous fluorescence emission before the endogenous fluorescence emission is detected by the camera; and
    a computer processor configured to analyze the endogenous fluorescence emission light and classify the endogenous fluorescence emission light as an indicator of endometrial tissue.

14. The apparatus of claim 13 wherein the LED is configured to emit excitation light with a wavelength of 450 nm.

15. The apparatus of claim 13 wherein the filter is a gradient-index (GRIN) lens.

16. The apparatus of claim 15 wherein the GRIN lens is configured to filter light below 550 nm.

17. The apparatus of claim 13 wherein the camera comprises a complementary metal-oxide-semiconductor (CMOS) sensor.

* * * * *

UNITED STATES PATENT AND TRADEMARK OFFICE
CERTIFICATE OF CORRECTION

| | |
|---|---|
| PATENT NO. | : 12,013,342 B2 |
| APPLICATION NO. | : 18/050902 |
| DATED | : June 18, 2024 |
| INVENTOR(S) | : Marc D. Feldman et al. |

It is certified that error appears in the above-identified patent and that said Letters Patent is hereby corrected as shown below:

In the Claims

Claim 13, Column 8, Line 39, delete "a wavelength between".

Signed and Sealed this
Sixteenth Day of July, 2024

Katherine Kelly Vidal
*Director of the United States Patent and Trademark Office*